United States Patent [19]

Kwun et al.

[11] Patent Number: 5,180,969
[45] Date of Patent: Jan. 19, 1993

[54] DETECTION OF REINFORCING STEEL CORROSION IN CONCRETE STRUCTURES USING NON-LINEAR HARMONIC AND INTERMODULATION WAVE GENERATION

[75] Inventors: Hegeon Kwun, San Antonio; Gary L. Burkhardt, Adkins; Jay L. Fisher, San Antonio, all of Tex.

[73] Assignee: Southwest Research Institute, San Antonio, Tex.

[21] Appl. No.: 830,702

[22] Filed: Feb. 4, 1992

[51] Int. Cl.$^5$ ............................................. G01N 27/00
[52] U.S. Cl. .............................. 324/71.2; 204/153.11; 324/240
[58] Field of Search ....................... 324/71.2, 425, 240, 324/337, 700; 204/153.11, 404; 455/40, 67.4; 364/484

[56] References Cited

U.S. PATENT DOCUMENTS

| | | | |
|---|---|---|---|
| 4,062,010 | 10/1977 | Young et al. | 343/5 |
| 4,072,942 | 2/1978 | Alongi | 343/5 |
| 4,099,117 | 7/1978 | Erath | 324/557 |
| 4,128,011 | 12/1978 | Savage | 73/579 |
| 4,238,298 | 12/1980 | Tsuru et al. | 324/700 |
| 4,658,365 | 4/1987 | Syrett et al. | 304/496 |
| 4,691,204 | 9/1987 | Hiramoto | 324/337 |
| 4,698,634 | 10/1987 | Alongi et al. | 342/22 |
| 4,703,253 | 10/1987 | Strommen | 324/65 |
| 4,703,255 | 10/1987 | Strommen | 324/65 |
| 4,706,031 | 11/1987 | Michiguchi | 324/337 |
| 4,812,850 | 3/1989 | Gunton et al. | 342/22 |
| 4,839,654 | 6/1989 | Ito et al. | 342/22 |
| 4,843,320 | 6/1989 | Spies | 324/240 |
| 4,940,944 | 7/1990 | Steele et al. | 324/425 |
| 5,006,786 | 4/1991 | McKubre et al. | 324/71.2 |
| 5,087,873 | 2/1992 | Murphy et al. | 324/71.2 |

Primary Examiner—Jack B. Harvey
Assistant Examiner—Maura K. Regan
Attorney, Agent, or Firm—Gunn, Lee & Miller

[57] ABSTRACT

A method for rapidly detecting and locating reinforcing steel corrosion in concrete structures using non-linear harmonic and intermodulated frequencies of electromagnetic signals. The method comprises transmitting either a single primary frequency or two primary frequencies into the concrete structure in the general direction of the reinforcing steel. The reflected/generated signal, which is composed of the primary frequencies and of various harmonics and intermodulation components, is received, filtered, and amplified. A third order harmonic frequency is isolated with a band pass filter, is amplified, and is compared with the amplitudes of the primary frequencies. Intermodulation frequencies, primarily the combination of the primary of a frequency and the second harmonic of a second frequency, or the primary of a second frequency and the second harmonic of a first frequency, are isolated by appropriate band pass filter, are amplified, and are compared with the primary frequency or frequencies. The comparative amplitudes of these harmonics or intermodulation frequencies are displayed and recorded, and are correlated with a degree of corrosion in the reinforcing steel.

12 Claims, 4 Drawing Sheets

Third Order Harmonic Measurement

Third Order Harmonic Measurement

Intermodulation Signal Measurement

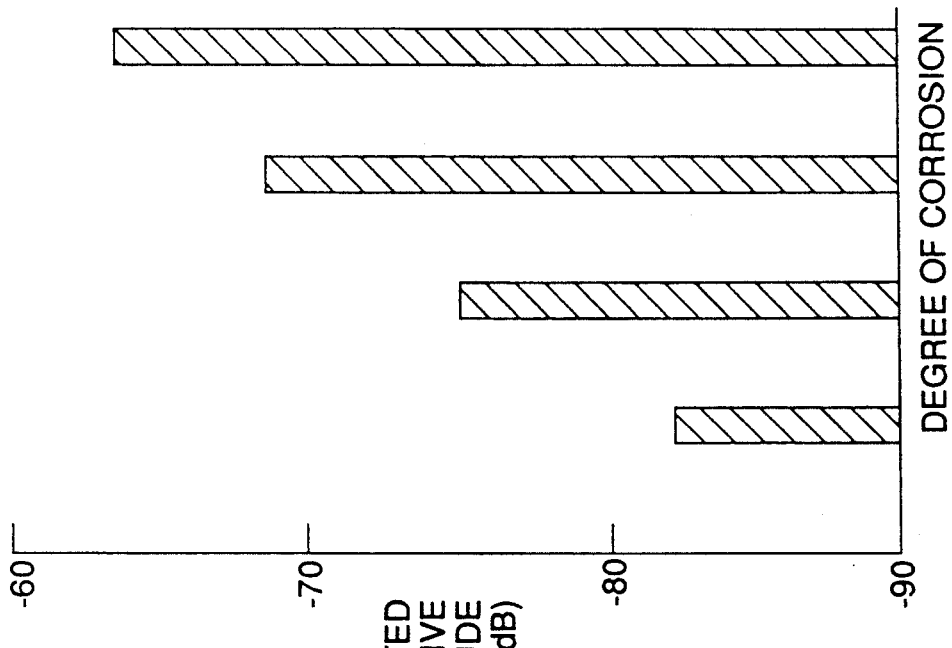
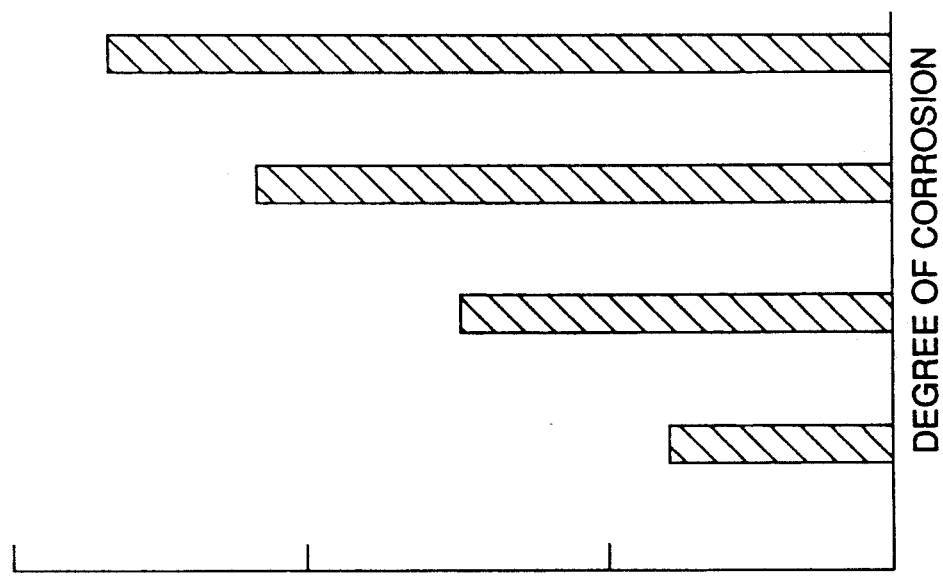

DETECTION OF REINFORCING STEEL CORROSION IN CONCRETE STRUCTURES USING NON-LINEAR HARMONIC AND INTERMODULATION WAVE GENERATION

BACKGROUND OF THE INVENTION

1. Field of the Invention

This invention relates generally to non-destructive methods of detecting and evaluating metallic corrosion. This invention relates more specifically to non-destructive methods for rapidly detecting and locating corrosion of reinforcing steel that occurs within concrete structures, by analyzing the non-linear harmonic and intermodulated frequencies of transmitted electromagnetic waves.

2. Description of Related Art

The utilization of concrete as a structure supporting and load bearing material has long been supplemented by the inclusion of reinforcing steel within the concrete. One of the unfortunate consequences of this inclusion, however, is the inevitable deterioration of the reinforcing steel when exposed to an intrusion of water, salt, oxygen, and other minerals that initiate chemical reactions. Not only can this deterioration of the reinforcing steel weaken its properties, it can exacerbate the deterioration of the concrete itself.

Reinforced concrete is utilized in numerous structures, including buildings, bridges, and other highway features. For this reason, it is important that engineers be able to determine the condition of reinforcing steel within concrete structures so as to assure their safety and reliability. It is also important to be able to obtain information on the integrity of reinforcing steel without the necessity of exposing it to visual inspection.

Presently, electrical potential measurements are widely used for monitoring the corrosive state of steel reinforcing bars in concrete. With these methods, the electrical potential between the steel reinforcement and a reference electrode, which is in physical contact with the surface of the concrete (if the concrete is dry, it must first be moistened), is measured using a voltmeter. These methods detect the presence of corrosive activity, but not the extent and location of corrosion damage. To make electrical potential measurements, a direct electrical connection must be made to the reinforcing steel. Therefore, if the steel is not exposed, some concrete covering must be removed.

Other methods that have been attempted include imbedding probes within the concrete structure adjacent to the reinforcing steel members so as to provide a means for returning at a later date, and making measurements with the probe to determine the rate or stage of deterioration. U.S. Pat. No. 4,703,255 and U.S. Pat. No. 4,703,253, both issued to strommen, describe particular embodiments of such a corrosion probe. Unfortunately, these probes must be installed at the time the concrete is poured in order to anticipate their use at a later date, and are useful only for that localized area.

There are many patented methods for utilizing electromagnetic waves, particularly in the radar frequencies, to detect and locate objects either under the ground or within concrete structures Some of these methods are disclosed in the following patents:

| Number | Patentee | Date | Title |
|---|---|---|---|
| 4,072,942 | Alongi | 02/07/78 | Apparatus for the Detection of Buried Objects |
| 4,691,204 | Hiramoto | 09/01/87 | Radar Apparatus |
| 4,698,634 | Alongi, et al | 10/06/87 | Subsurface Inspection Radar |
| 4,706,031 | Michiguchi, et al | 11/10/87 | Method and System for Detecting an Object with a Radio Wave |
| 4,839,654 | Ito, et al | 06/13/89 | System for Detecting Underground Objects |

The utilization of radar, and of any other electromagnetic radiation for that matter, has generally been limited to the detection and location of reinforcing components within concrete structures, rather than an actual analysis of the stage of deterioration these reinforcing components are in.

Metal-to-metal junctions that are separated by thin, non-metallic materials such as oxides, are known to exhibit non-linear electrical behaviors Examples of these kinds of junctions include metal-to-metal contacts, corrosion, stress corrosion cracks, and fatigue cracks. Because of the antisymmetry of the voltage-current curve associated with these junctions, the non-linear effects produced are odd numbered with the third order effects being predominant. This phenomenon is well known in the fields of electronics and telecommunications, since it is a source of undesired noise.

When metal-to-metal junctions are excited at two frequencies, harmonics (HM) and intermodulation (IM) frequencies are generated due to the non-linear effects of the junction. For example, when these junctions are excited at frequencies $f_1$, and $f_2$, the HM and IM signals generated include $3f_1$, $3f_2$, $f_1 \pm 2f_2$, $2f_1 \pm f_2$, etc. The corrosion of such junctions significantly enhances this effect and thus the noise problem associated with these junctions. Both the HM and IM signals increase in amplitude as the degree of corrosion increases.

The utilization of these HM and IM signals that are generated by corroded contacts has been limited primarily to their detection and elimination from electronic equipment, where their presence adds to the background noise levels.

SUMMARY OF THE INVENTION

Because the corrosion of reinforcing steel creates metal-to-metal "junctions" that are similar in many respects to the metal-to-metal contacts that are found in electronics equipment, it is conceivable that the presence of HM and IM frequency components could be utilized to make quantitative measurements of the corrosion of reinforcing steel without direct contact with the steel. Removal of the surrounding concrete is, therefore, avoided.

It is therefore an object of the present invention to provide a method for determining the presence of metallic corrosion on reinforcing steel members within concrete structures.

It is a further object of the present invention to provide a method for determining the presence of corrosion on reinforcing steel members within concrete structures that is non-destructive of the concrete structure.

It is a further object of the present invention to provide a method for detecting and locating corrosion of steel reinforcing members within concrete structures that utilizes HM and IM electromagnetic signals in a manner that obviates the need for direct access to the steel reinforcing members.

It is a further object of the present invention to provide a method of detecting and locating corrosion of steel reinforcing members within concrete structures that utilizes HM and IM electromagnetic signals, and that eliminates problems associated with spuriously generated and reflected electromagnetic signals.

In fulfillment of these and other objectives, the present invention provides a first frequency signal transmitter, or a first and a second frequency signal transmitter, which radiate monochromatic electromagnetic waves toward reinforcing steel members within concrete structures The method of the present invention then detects the HM and IM electromagnetic waves generated, which result from the illumination of the reinforcing steel by the transmitted signals. The method of the present invention then correlates an increased amplitude of the generated HM and IM components with a degree of corrosion found within the steel reinforcing members. Other objects and advantages of the present invention will become apparent from the following detailed description and drawing.

BRIEF DESCRIPTION OF THE DRAWINGS

FIG. 5 is a graph of the third harmonic frequency amplitude relative to the fundamental frequency amplitude in decibels versus the relative degree of corrosion found in the reinforcing steel.

FIG. 6 is a graph of the intermodulated frequencies amplitude relative to the fundamental frequency amplitude in decibels versus the relative degree of corrosion found in the reinforcing steel.

DETAILED DESCRIPTION OF THE PREFERRED EMBODIMENT

Figure 1:
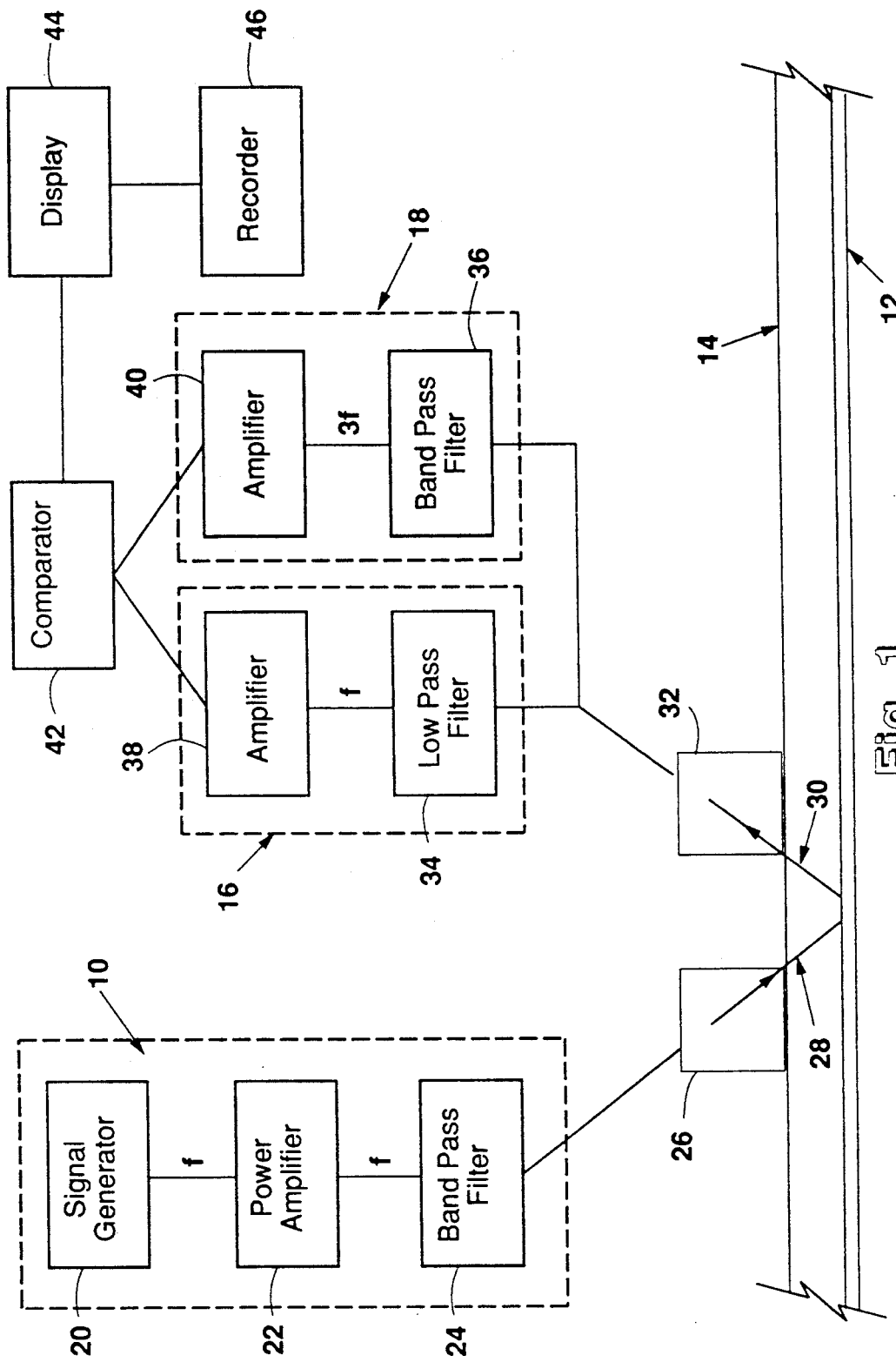
FIG. 1 a schematic block diagram of a preferred embodiment of the present invention shown appropriately configured to measure the amplitude of third harmonic frequencies.

Reference is made first to FIG. 1 for a detailed description of a system suitable for carrying out the method of a preferred embodiment wherein third order harmonic frequencies are measured and compared with the reflected fundamental frequency.

Signal transmitter 26 and signal detector 32 are placed in a position proximate to reinforcing steel 12 contained within concrete structure 14.

Signal transmitter 26 is energized by power generator which is comprised of signal generator 20, power amplifier 22, band pass filter 24 to create a monochromatic wave. Signal transmitter 26 then radiates the monochromatic wave 28 into concrete structure 24 in a direction that allows it to be intercepted by reinforcing steel 12.

Reflected/generated signal 32 is made up of the reflected fundamental frequency transmitted as well as any harmonic (HM) and intermodulated (IM) frequencies that are generated by the corrosive factors associated with reinforcing steel 12. This reflected/generated signal 30 is detected by signal detector 32, and is processed through both fundamental frequency receiver 16 and third HM frequency receiver 18. Fundamental frequency receiver 16 is comprised of low pass filter 34, which isolates the fundamental frequency and carries it to amplifier 38. Third HM frequency receiver 18 comprises band pass filter 36, which selects, in this case, a third HM of the fundamental frequency. This third HM frequency signal is amplified by amplifier 40.

The two amplified signals are then analyzed by comparator 42 to determine the amplitude and/or phase of the third HM component relative to that of the fundamental frequency component. Band pass filters 34 and 36, amplifiers 38 and 40, as well as comparator 42 may all be incorporated in a standard frequency analyzer unit rather than being connected as discrete components. A number of readily available frequency analyzes are capable of providing the amplification, filtering, and analysis required.

The relative amplitude analysis is then displayed on display 44 and may optionally be recorded by recorder 46. Display 44 and recorder 46 may be functional components of a standard personal computer unit that may facilitate the display and analysis of the data.

It is the relative amplitude that provides a quantitative determination of the degree of corrosion on reinforcing steel 12. The reinforcing steel, because of its magnetic hysterisis, also generates HM and IM signals. To detect corrosion related HM and IM signals, it may be necessary to minimize those HM and IM signals from the material by applying a high bias DC magnetic field to magnetically saturate the material.

Figure 2:
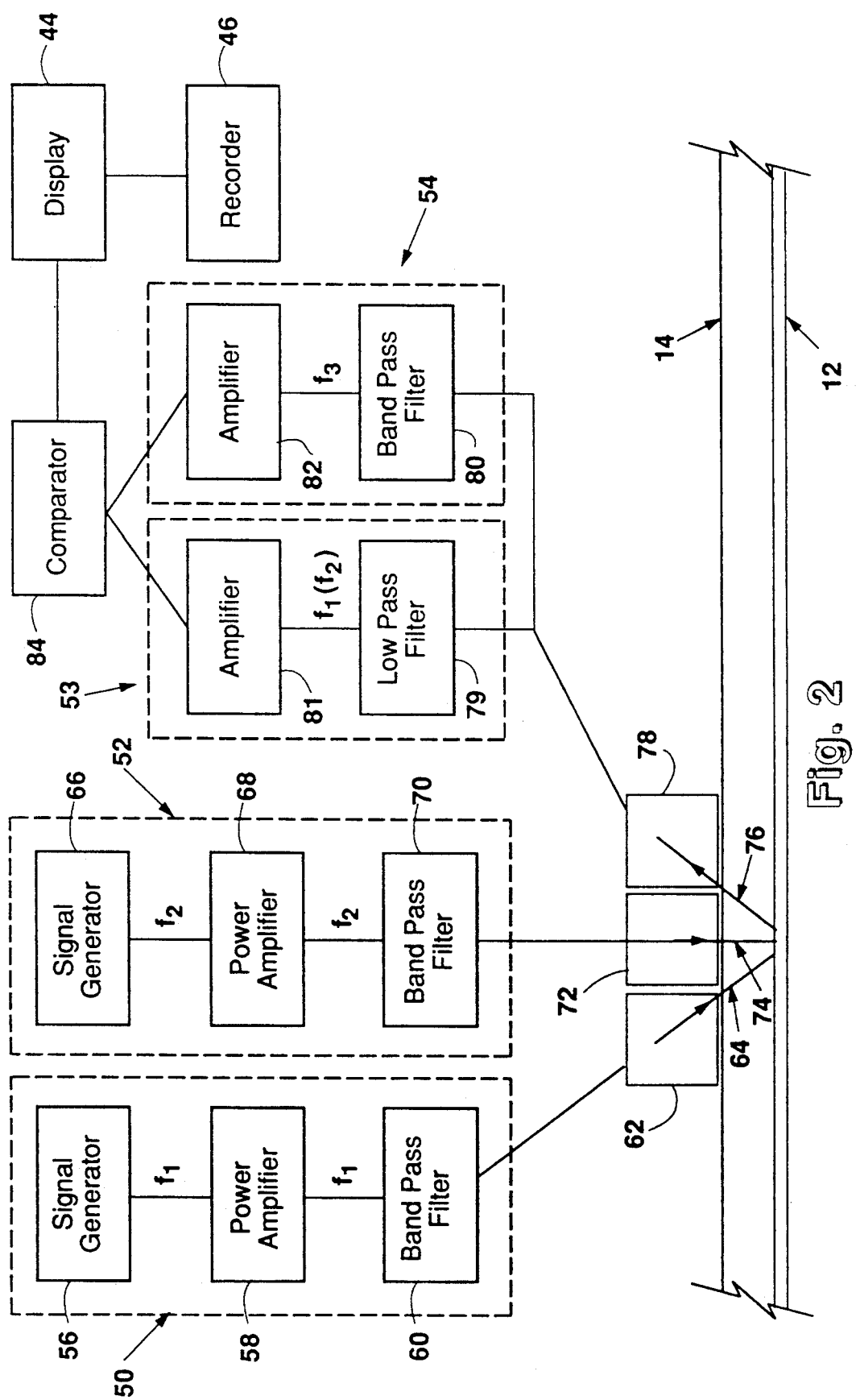
FIG. 2 a schematic block diagram of a preferred embodiment of the present invention shown appropriately configured to measure the amplitude of intermodulated frequencies.

Reference is now made to FIG. 2 for an alternative arrangement of the system shown in FIG. 1, in which IM signals are gathered and analyzed rather than the third HM signals that are analyzed with the system of FIG. 1.

In FIG. there are two signal transmitters, first frequency signal transmitter 62, and second frequency signal transmitter 72. As with signal transmitter 26 shown in FIG. 1, first and second frequency signal transmitters 62 and 72 in FIG. 2, provide selected frequencies and direct these waves at reinforcing steel 12 imbedded within concrete structure 14. Reflected/generated signal 76 is then received by reflected signal receiver 78.

First frequency signal transmitter 72 is energized by power generator 52 which is comprised of first frequency signal generator 56, (which provides a frequency f), first frequency signal amplifier 58, and band pass filter 60. Power generator 50 provides a monochromatic first frequency signal 64 to be transmitted and reflected off of reinforcing steel 12 to become a component of reflected/generated signal 76.

Second frequency signal transmitter 72 is energized by power generator 52 which is comprised of second frequency signal generator 66, (which provides a frequency $f_2$ distinct from first frequency $f_1$), second frequency signal amplifier 68, and band pass filter 70. Power generator 52 provides a second monochromatic frequency signal, which is transmitted by second frequency signal transmitter 72 in a direction that allows it to combine with first frequency signal 64 to impinge upon reinforcing steel 12. Second frequency signal 74 and first frequency signal 64 are reflected off of reinforcing steel 12, and cause the generation of HM and IM frequencies. All of these components make up reflected/generated signal 76, which is received by reflected signal receiver 78. The reflected/generated signal is then conducted to fundamental frequency signal receiver 53 and IM frequency signal receiver 54, where the fundamental and IM components of signal 76 are selected out by low pass and band pass filters 79 and 80. These fundamental and IM signal components are then amplified by signal amplifiers 81 and 82, and the amplitudes of the IM signal components are compared to the amplitudes of the first fundamental frequency ($f_1$) and the second fundamental frequency ($f_2$) by comparator 84. The amplitude differences are then determined, as with the third HM method, to be indicative of a degree of corrosion on reinforcing steel 12 The amplitude differences are then displayed and optionally recorded as with the third HM method.

Figure 3:
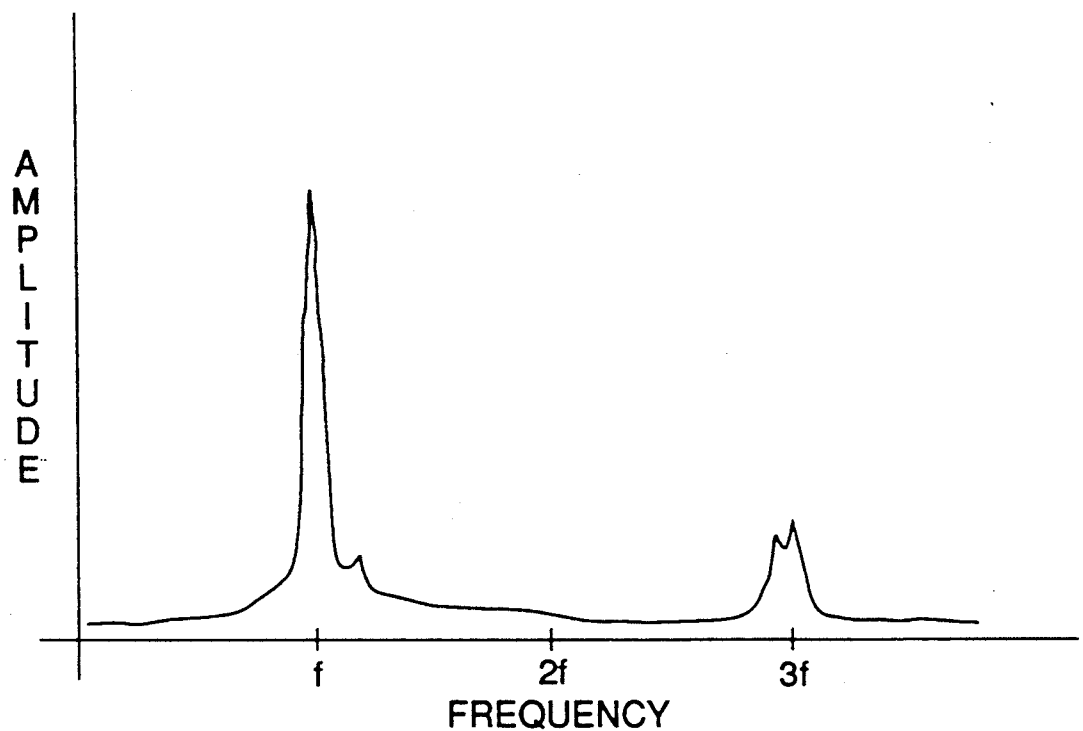
FIG. 3 is a graph of frequency versus amplitude showing the signal characteristics of reflected signal 30 shown in FIG. 1.
Figure 4:
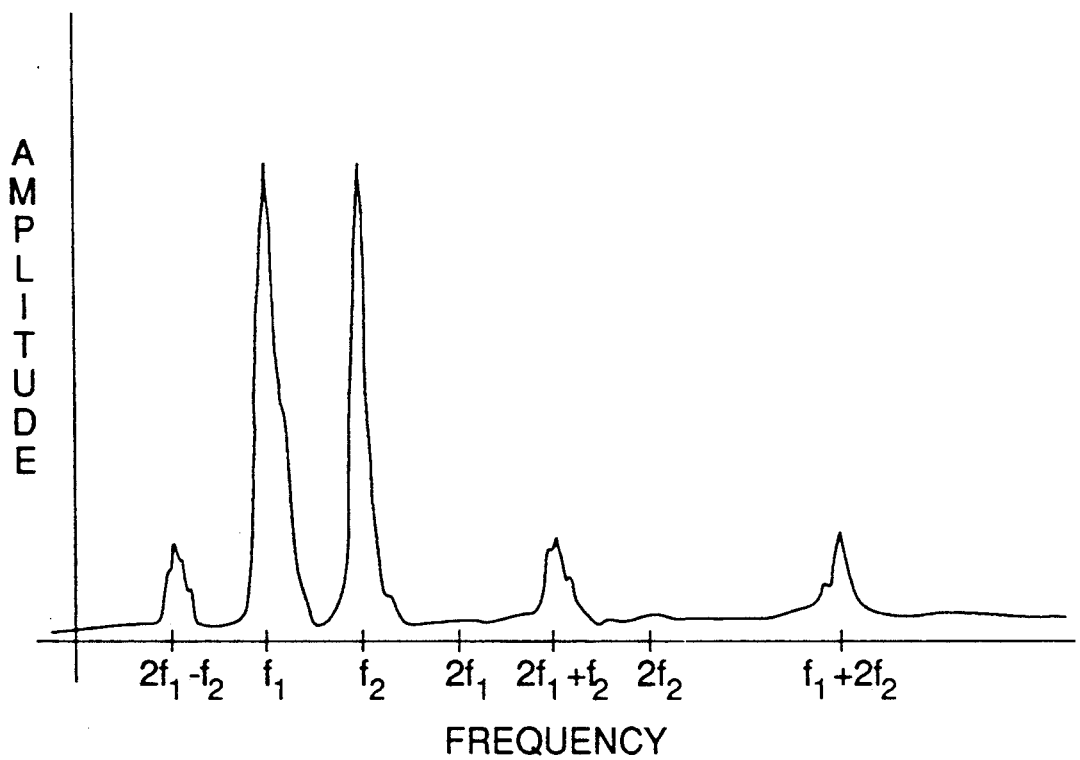
FIG. 4 is a graph of frequency versus amplitude showing the signal characteristics of reflected signal 76 shown in FIG. 2.

FIGS. 3 and 4 of the drawing demonstrate the frequency distribution of the received reflected/generated signals from reinforcing steel 12. FIG. 3 is a graphic representation of reflected/generated signal 30, and shows the frequency spectrum of the signal versus the various frequencies' relative amplitudes. Because of the non-linearity of the corrosive junctions in reinforcing steel 12, HM frequencies are generated in amplitudes that are proportional to the degree of corrosion. In FIG. 3 for a moderately corroded steel member, the reflected/generated signal indicates the expected high amplitude at the fundamental frequency as well as a measurable amplitude at the HM frequency. It is the process of comparing this amplitude of the fundamental frequency, and that of third HM frequency that allows for a determination of the degree of corrosion to be found in the reinforcing steel 12.

FIG. 4 is a plot similar to that of FIG. 3, wherein the IM signal components found in reflected/generated signal 76 of FIG. 2 are graphically displayed. The fundamental frequencies $f_1$ and $f_2$, as expected, are shown to have significant amplitudes. An array of lower amplitudes, however, are found for a number of other frequencies shown to be first order IM frequencies. In FIG. 4, these IM frequencies are indicated as $2f_1 \pm f_2$, and $f_1 \pm 2f_2$. Other IM frequencies may occur, but their amplitudes are not as significant as those of the third order IM frequencies. As with the third HM frequencies, these IM frequencies have been found to increase in amplitude with a corresponding increase in a degree of corrosion in the reinforcing steel 12. By comparing the amplitude of the IM frequencies to the amplitudes of the fundamental frequencies, this degree of corrosion can be determined.

Initially, a reference standard for the amplitude of the third HM and IM frequencies generated by reinforcing steel 12 within concrete structure 14 should be obtained. Reference measurements using a non-corroded reinforcing steel member may be obtained and used as a standard against which subsequent measurements of third HM and IM frequency amplitudes can be compared. For example, a reference measurement may identify a relative amplitude of −80 decibels for the generated frequencies relative to the fundamental component of the reflected signal. Thereafter, tests which indicate anything more than the standard value would point to a corresponding degree of corrosion to be found within the steel reinforcing member. Quantitative measurements of clean, slightly corroded, moderately corroded, and severely corroded reinforcing steel members have been made which indicate a progressive increase in the relative amplitudes of the third HM or IM frequency components, and the fundamental frequency components.

Graphs of these variations in amplitudes that have been obtained using lower frequency radar transmissions are shown in FIGS. 5 and 6. In FIG. 5, the relative amplitude of the third HM components of the reflected/generated signals are compared with the reflected fundamental frequency component of the reflected signal. In FIG. 6, a similar graph shows the relative amplitudes of the IM frequencies with respect to the fundamental frequency component.

For simplicity, when two frequencies are transmitted and a first set of IM frequencies is received, the amplitudes of each of the fundamental frequencies should be the same. This simplifies the correlation between a relative difference in amplitude and a degree of corrosion.

It may be that under certain conditions as where the concrete structure is saturated with water, a measure of the IM frequencies would provide a better correlation with the degree of corrosion then the third HM method, or vis versa. Either method may, however, be utilized under any condition as long as a standard reference value for the absence of corrosion has been determined in advance.

Although the preferred embodiment of the present invention has been described in detail, its detailed description should not be construed as limiting the scope, but merely providing illustrations of some of the presently preferred embodiments of this invention. In addition, the present invention might be applied to structures other than those made of concrete, which incorporate reinforcing members which have a propensity towards corrosion. Thus, the scope of the present invention should be determined by the appended claims rather than by these specific examples described herein above.

I claim:

1. A method of detecting corrosion on an electrically conductive member that is surrounded by an electrically non-conductive material and is unavailable to visual inspection, comprising the steps of:
  transmitting a first electromagnetic signal through said electrically non-conductive material so as to illuminate said electrically conductive member, said first electromagnetic signal having at least one fundamental frequency;
  receiving a reflected/generated electromagnetic signal from said electrically conductive member within said electrically non-conductive material, said reflected/generated electromagnetic signal comprising a reflected component made of said fundamental frequency and a generated component made of a plurality of harmonic and intermodulated frequencies of said fundamental frequency, said harmonics and intermodulated frequencies being ten rated by non-linear electrical characteristics attributable to said corrosion of said electrically conductive member, said step of receiving said signal comprising the steps of:
  positioning a receiver so as to intercept said reflected/generated electromagnetic signal from said electrically conductive member within said electrically non-conductive material;
  filtering said reflected/generated electromagnetic signal with a band pass filter and with a low pass filter so as to separate said reflected component made of said fundamental frequency from said generated component made of said plurality of harmonic and intermodulated frequencies;

amplifying said reflected component of said reflected/generated electromagnetic signal at said fundamental frequency with an electronic power amplifier; and amplifying said generated component of said reflected/generated electromagnetic signal at said at said plurality of harmonic and intermodulated frequencies with an electronic power amplifier; and determining a relative amplitude of said generated component of said reflected/generated electromagnetic signal in relation to said reflected component of said reflected/generated electromagnetic signal;

wherein said reflective amplitude is indicative of a degree of said corrosion in said electrically conductive member.

2. A method of detecting corrosion on an electrically conductive member that is surrounded by an electrically non-conductive material and is unavailable to visual inspection, comprising the steps of;

transmitting a first electromagnetic signal through said electrically non-conductive material so as to illuminate said electrically conductive member, said first electromagnetic signal having at least one fundamental frequency;

receiving a reflected/generated electromagnetic signal from said electrically conductive member within said electrically non-conductive material, said reflected/generated electromagnetic signal comprising a reflected component made of said fundamental frequency and a generated component made of a plurality of harmonic and intermodulated frequencies of said fundamental frequency, said harmonics and intermodulated frequencies being generated by non-linear electrical characteristics attributable to said corrosion of said electrically conducive member; and determining a relative amplitude of said generated component of said reflected/generated electromagnetic signal in relation to said reflected component of said reflected/generated electromagnetic signal, said step of determining a relative amplitude comprising the steps of;

comparing an amplitude of said generated component of said reflected/generated electromagnetic signal at said plurality of harmonic and intermodulated frequencies with an amplitude of is reflected component of said reflected/generated electromagnetic signal at said fundamental frequency by way of an electronic comparator;

determining a quantitative difference between said amplitude of said generated component and said amplitude of said reflected component; and correlating said quantitative difference with a degree f corrosion on said metallic member;

wherein said relative amplitude is indicative of a degree of said corrosion in said electrically conducive member.

3. A method of detecting and locating corrosion in reinforcing steel within a concrete structure comprising the steps of:

positioning an electromagnetic signal transmitter adjacent to said concrete structure, wherein said concrete structure is known to contain said reinforcing steel;

generating a first electromagnetic signal with said electromagnetic signal transmitter, said electromagnetic signal having a first frequency, and having an amplitude;

transmitting said first electromagnetic signal through said concrete structure so as to illuminate said reinforcing steel;

reflecting said first electromagnetic signal off of said reinforcing steel;

causing the generation of a second electromagnetic signal from said reinforcing steel, said second electromagnetic signal comprising a plurality of harmonics and intermodulation frequencies of said first frequency, said second electromagnetic signal being generated by non-linear electrical characteristics attributable to said corrosion of said reinforcing steel, said second electromagnetic signal having an amplitude;

positioning an electromagnetic signal receiver adjacent to said concrete structure, wherein said first electromagnetic signal has been transmitted;

receiving said reflected first electromagnetic signal and said generated second electromagnetic signal from said reinforcing steel in said concrete structure;

separating said first frequency of said reflected first electromagnetic signal from said plurality of harmonic and intermodulated frequencies of said first frequency within said generated second electromagnetic signal; and comparing said amplitude of said first frequency of said reflected first electromagnetic signal with said amplitude of said plurality of harmonic and intermodulated frequencies of said generated second electromagnetic signal;

wherein a difference between said amplitude of said first frequency of said reflected first electromagnetic signal, and said amplitude of said plurality of harmonic and intermodulated frequencies of said generated second electromagnetic signal is indicative of a degree of corrosion in said reinforcing steel.

4. The method of claim 3, wherein said step of generating a first electromagnetic signal comprises the steps of:

creating said first electromagnetic signal at said first frequency with an electronic signal generator;

amplifying said first electromagnetic signal at said first frequency with an electronic power amplifier; and filtering said first electromagnetic signal at said first frequency with a band pass filter;

wherein said band pass filter selects and passes said first electromagnetic signal at said first frequency.

5. The method of claim 3, wherein said first frequency of said first electromagnetic signal is in the radar range of the electromagnetic frequency spectrum.

6. The method of claim 3, wherein said step of separating said first frequency from said harmonic and intermodulated frequencies comprises:

filtering said reflected first electromagnetic signal and said generated second electromagnetic signal with a low pass filter so as to separate out said first frequency;

filtering said reflected first electromagnetic signal and said generated second electromagnetic signal with a band pass filter so as to separate out a third harmonic of said first frequency;

amplifying said first frequency and said third harmonic frequency;

comparing said amplitude of said first frequency with said amplitude of said third harmonic frequency;

determining a difference between said amplitude of said first frequency and said amplitude of said third harmonic frequency; and correlating a difference between said amplitude of said first frequency and said amplitude of said third harmonic frequency with a degree of corrosion in said reinforcing steel.

7. The method of claim 3 further comprising the step of obtaining a reference standard third harmonic and intermodulated frequency amplitude indicative of an absence of corrosion in said reinforcing steel.

8. A method of detecting and locating corrosion in reinforcing steel within a concrete structure comprising the steps of:

positioning a first electromagnetic signal transmitter adjacent to said concrete structure, wherein said concrete structure is known to contain said reinforcing steel;

generating a first electromagnetic signal with said electromagnetic signal transmitter, said electromagnetic signal having a first frequency, and having an amplitude;

transmitting said first electromagnetic signal through said concrete structure so as to illuminate said reinforcing steel;

positioning a second electromagnetic signal transmitter adjacent to said concrete structure, wherein said concrete structure is known to contain said reinforcing steel;

generating a second electromagnetic signal with said electromagnetic signal transmitter, said electromagnetic signal having a second frequency, and having an amplitude;

transmitting said second electromagnetic signal through said concrete structure so as to illuminate said reinforcing steel;

reflecting said first and said second electromagnetic signals off of said reinforcing steel;

causing the generation of a third electromagnetic signal from said reinforcing steel, said third electromagnetic signal comprising a plurality of harmonics and intermodulation frequencies of said first and said second frequencies, said third electromagnetic signal being generated by non-linear electrical characteristics attributable to said corrosion of said reinforcing steel, said third electromagnetic signal having an amplitude;

positioning an electromagnetic signal receiver adjacent to said concrete structure, wherein said first and said second electromagnetic signals have been transmitted;

receiving said reflected first and second electromagnetic signals and said generated third electromagnetic signal from said reinforcing steel in said concrete structure;

separating said first and second frequencies of said reflected first and second electromagnetic signals from said plurality of harmonic and intermodulated frequencies of said generated third electromagnetic signal; and comparing said amplitudes of said first and second frequencies with said amplitudes of said plurality of harmonic and intermodulated frequencies;

wherein a difference between said amplitudes of said first and second frequencies, and said amplitudes of said plurality of harmonic and intermodulated frequencies is indicative of a degree of corrosion in said reinforcing steel.

9. The method of claim 8, wherein said step of generating a first electromagnetic signal comprises the steps of:

creating said first electromagnetic signal at said first frequency with an electronic signal generator;

amplifying said first electromagnetic signal at said first frequency with an electronic power amplifier;

filtering said first electromagnetic signal at said first frequency with a band pass filter, wherein said band pass filter selects and passes said first electromagnetic signal at said first frequency; and said step of generating a second electromagnetic signal comprises the steps of:

creating said second electromagnetic signal at said second frequency with an electronic signal generator;

amplifying said second electromagnetic signal at said second frequency with an electronic power amplifier; and filtering said second electromagnetic signal at said second frequency with a band pass filter, wherein said band pass filter selects and passes said second electromagnetic signal at said second frequency.

10. The method of claim 8, wherein said first frequency of said first electromagnetic signal and said second frequency of said second electromagnetic signal are in the radar range of the electromagnetic frequency spectrum.

11. The method of claim 8, wherein said step of separating said first and said second frequencies from said harmonic and intermodulated frequencies comprises:

filtering said reflected first and second electromagnetic signals and said generated third electromagnetic signal with a low pass filter so as to separate out said first and second frequencies;

filtering said reflected first and second electromagnetic signals and said generated third electromagnetic signal with a band pass filter so as to separate out at least one intermodulated frequency of said first and second frequencies;

amplifying said first and second frequencies and said intermodulated frequency;

comparing said amplitude of said first and second frequencies with said amplitude of said intermodulated frequency;

determining a difference between said amplitude of said first and second frequencies and said amplitude of said intermodulated frequency; and correlating a difference between said amplitude of said first and second frequencies and said amplitude of said intermodulated frequency with a degree of corrosion in said reinforcing steel.

12. The method of claim 8 further comprising the step of obtaining a reference standard third harmonic and intermodulation frequency amplitude indicative of an absence of corrosion in said reinforcing steel.

* * * * *